(12) United States Patent
Sills et al.

(10) Patent No.: US 6,581,014 B2
(45) Date of Patent: Jun. 17, 2003

(54) APPARATUS AND METHOD FOR ANALYSIS OF GUIDED ULTRASONIC WAVES

(75) Inventors: James A. Sills, San Antonio, TX (US); Christian J. Schwartz, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/828,640

(22) Filed: Apr. 9, 2001

(65) Prior Publication Data

US 2002/0029116 A1 Mar. 7, 2002

Related U.S. Application Data (60) Provisional application No. 60/219,762, filed on Jul. 20, 2000.

(51) Int. Cl.[7] .................................. G01B 5/28
(52) U.S. Cl. ....................................... 702/39
(58) Field of Search ............... 702/39; 73/644, 73/622, 637, 618, 602; 235/151; 128/660

(56) References Cited

U.S. PATENT DOCUMENTS 3,674,998 A * 7/1972 Benz ...................... 235/151.3
4,290,308 A    9/1981 Dau
4,665,924 A * 5/1987 Saito et al. ................. 128/660
5,691,476 A * 11/1997 Madaras ...................... 73/644

* cited by examiner

Primary Examiner—John Barlow
Assistant Examiner—Tung S Lau
(74) Attorney, Agent, or Firm—Gunn, Lee & Hanor (57) ABSTRACT

Method and apparatus for using a guided wave to determine the location of one or more flaws in an inspected object are disclosed. An ultrasonic guided wave is launched into the object using conventional ultrasound methods, and the reflected/received guided wave is sampled to capture a series of individual reflected waveforms. The individual reflected waveforms are then partitioned according to the sampling time. Each of the partitioned acquired waveforms is compared with a selected time-varying dispersion-modeled reference waveform associated with the unique geometry of the inspected object, a multiplicity of "theoretical" flaw locations, and the characteristics of the original ultrasonic guided wave. To make a comparison, the reference waveform is also generated as a series of partitioned waveforms which model the shape of a wave that may be expected to be reflected from a multiplicity of theoretical flaws located in the object. The shape of the reflected waveforms is correlated with the shape of the reference waveforms, and a high level of correlation indicates the presence of a real flaw at the theoretical flaw location.

19 Claims, 7 Drawing Sheets

APPARATUS AND METHOD FOR ANALYSIS OF GUIDED ULTRASONIC WAVES

REFERENCE TO RELATED APPLICATIONS

This application claims the benefit of U.S. Provisional Application for Patent No. 60/219,762 titled "Time-Varying Matched Filter Method for Analysis of Guided Ultrasonic Waves" filed on Jul. 20, 2000, is related thereto, is commonly assigned therewith, and the subject matter thereof is incorporated herein by reference in its entirety.

BACKGROUND OF THE INVENTION

1. Technical Field

This invention relates generally to nondestructive testing and, more particularly, to a method and apparatus for analyzing guided waves in inspected objects using time-varying matched filters.

2. History of Related Art

Ultrasonic wave inspection techniques are useful for many Non-Destructive Evaluation (NDE) applications. These techniques typically involve transmitting a narrow band ultrasonic frequency interrogation signal down the length of an object and analyzing the reflected or "inspection" signal for the presence of material boundaries or flaws (e.g., surfaces, joints, welds, cracks, etc.) in the object. Defects in the object that cannot be seen by visual inspection can often be detected by analyzing the inspection signal. Thus, ultrasonic wave inspection techniques can provide a cost effective solution for detecting defects in many objects such as railroad rails, stranded cables, pipes, and the like, from a single set up location.

Generally, in the field of acoustics, there are two fundamental types of waves that propagate through material: pressure waves, and shear waves. These waves are called "bulk" waves and they propagate through the material at a constant velocity over all frequencies, including ultrasonic frequencies. An incident ultrasonic bulk wave transmitted along an object will be reflected from one end of the object so as to arrive at a fixed time at the transmission location according to a predictable, fixed travel time period.

Ultrasonic bulk waves are typically used as the incident waves in non-destructive evaluation applications. As the bulk waves enter an object and propagate along the length thereof, they reflect between the surfaces of the object. In objects of continuous cross section, the interaction of the bulk waves with one another and the object's surfaces produces envelopes of disturbance, called Lamb waves or guided waves, which also propagate along the object. Guided waves, unlike bulk waves, have velocities that vary depending on the frequency components of the waves. Thus, the time of arrival for a guided wave envelope reflected from the end of a pipe is often different for each envelope.

Furthermore, whereas there are only two types of bulk waves, there are an infinite number of guided waves that can exist for an object of a given geometry, such as a pipe. These different types of guided waves are distinguished by their modes; each mode has its own velocity vs. frequency relationship. Moreover, in a typical guided wave inspection, it is virtually impossible to ensure that only one mode will propagate. To the contrary, it is more likely that two or more modes will be present, thereby producing multiple reflections from the same material boundary or flaw, each having different velocities and, therefore, different times of arrival.

The phenomenon of the velocity of a signal being dependent on its frequency is called "dispersion." The effect of dispersion on guided waves is to cause their waveforms to change with time, generally becoming more elongated as they propagate down the length of the examined object. Guided waves have varying amounts of dispersion depending on the wave mode. For example, "longitudinal-one" or L(0, 1) guided waves are dispersive over virtually all frequencies, whereas "longitudinal-two" or L(0, 2) guided waves have a short band of frequencies over which they are not dispersive. Within this short band of frequencies, the velocity of the L(0, 2) guided wave is essentially constant and, therefore, the distance traveled over a given time period may be more readily determined. For this reason, L(0, 2) guided waves are commonly used in locating flaws and defects in piping.

Distinguishing guided wave modes among multiple reflections, however, can be quite a complicated process. As mentioned previously, guided waves of many different modes are produced by the interaction of bulk waves with object boundaries and flaws. The presence of these modes can lead to multiple detections of the same boundary or flaw within the object and different levels of sensitivity to the boundary or flaw based on the specific reflected mode. The presence of noise in the inspection signal can mask reflections to make the task of identifying individual modes even more difficult. Analysis of the inspection signal can therefore become a very complex task that requires extensive knowledge and time.

Conventional methods used to analyze guided wave inspection signals apply joint time-frequency analysis techniques in an attempt to observe dispersive behavior in reflected guided waves and then match the behavior to the modes theoretically predicted by such behavior. However, the time when a reflection begins (i.e., the onset of reflection) can be unclear, and dispersion of the narrow frequency band initiation pulse used to produce guided waves tends to decrease resolution due to elongation or "widening" of the waveform over time. Furthermore, a dispersive guided wave mode can sometimes appear to be non-dispersive, such that a portion of the L(0, 1) mode may resemble a portion of the L(0, 2) mode.

One commonly used joint time-frequency analysis technique is the Short-Time Fourier Transform (STFT). The STFT display, or spectrogram, can make evident velocity differences between frequency components of an examined portion of the inspection signal. The STFT provides useful results, but has several limitations. First, due to its limited resolution in both the time and frequency domains, the STFT result becomes difficult to accurately interpret as the distance traveled by the guided wave increases. As mentioned earlier, dispersive guided wave modes elongate in the time domain as they propagate down the length of the examined object. The resulting elongated shape in the STFT can interfere with other reflections. The presence of noise in the signal further complicates STFT interpretation. Therefore, techniques based on the STFT can have difficulty pinpointing the exact onset of a reflection signal due to the limited resolution of the STFT. Thus, analysis of the STFT typically requires tedious labor by skilled analysts with extensive experience, and is difficult to automate.

Accordingly, it is desirable to provide a more reliable and robust method and apparatus for analyzing guided wave inspection signals. Specifically, it is desirable to provide a signal processing method and apparatus that can more effectively accommodate the dispersive nature of guided wave modes so as to aid in the reliable characterization of inspected object geometric boundaries and flaws.

SUMMARY OF THE INVENTION

The present invention is directed to a method and apparatus for analyzing guided waves using a time-varying matched filter to correlate received guided waves with a time-varying dispersion-modeled reference wave to determine the location of a real flaw in an inspected object.

In general, in one aspect, the method includes the steps of selecting a time-varying dispersion-modeled reference signal associated with the geometry of an inspected object, a multiplicity of theoretical flaw locations located within the inspected object, and one or more characteristics of the selected guided wave; launching the selected guided wave signal into the inspected object; receiving a reflected signal generated by the interaction of the selected guided wave and the geometry of the inspected object (including any real flaw located therein); comparing the time-varying dispersion-modeled reference signal with the received reflected signal; and determining the location of the real flaw in the inspected object if the time-varying dispersion-modeled reference signal is substantially similar to the received reflected signal. The comparison can be conducted over the entire waveform for the reference and reflected signals during each sample interval. The comparison can also be conducted using only the detected wave envelope for each reference and reflected signal.

In general, in another aspect, the apparatus includes a means for selecting a time-varying dispersion-modeled reference signal associated with the geometry of an inspected object, a multiplicity of theoretical flaw locations located within the object, and the characteristics of the selected guided wave; a means for launching the selected guided wave signal into the inspected object; a means for receiving a reflected signal generated by the interaction of the selected guided wave and the geometry of the inspected object; a means for comparing the time-varying dispersion-modeled reference signal with the received reflected signal; and a means for determining the location of a real flaw in the inspected object if the time-varying dispersion-modeled reference signal is substantially similar to the received reflected signal.

The means for selecting the time-varying dispersion-modeled reference signal associated with the geometry of the inspected object, the multiplicity of theoretical flaw locations, and the characteristics of the guided wave may include a workstation or desktop computer capable of simulating the dispersive behavior of a guided wave in the inspected object, such as a pipe, as it interacts with the geometry of the inspected object. The computer typically includes a memory unit, a processor unit, and a storage unit for storing one or more program modules to generate individual reference signals which correspond to each sample of the reflected signal to be compared.

The means for launching the guided wave signal into the inspected object and the means for receiving the reflected signal generated by the interaction of the guided wave and the geometry of the inspected object may be an ultrasonic signal generator and a transducer, respectively.

The means for comparing the time-varying dispersion-modeled reference signal with the reflected signal and the means for determining the location of the real flaw in the inspected object if the time-varying dispersion-modeled reference signal is substantially similar to the reflected signal may also comprise a desktop computer, workstation, or other data processing apparatus, as are well known to those skilled in the art.

The method and apparatus operate under the assumption that a theoretical flaw exists at every point in time during which a waveform is acquired. If the waveform of the acquired reflected signal has a high level of correlation with the waveform of the generated reference signal corresponding to that point in time, then the hypothesis or assumption of a flaw at that location in the inspected object is verified. If there is a low level of correlation, then the hypothesis fails, and no flaw is detected.

BRIEF DESCRIPTION OF THE DRAWINGS

A more complete understanding of the method and apparatus of the present invention may be had by reference to the following detailed description when taken in conjunction with the accompanying drawings wherein.

DETAILED DESCRIPTION OF PRESENTLY PREFERRED EXEMPLARY EMBODIMENTS

Following is a detailed description of the preferred embodiments of the present invention and its advantages with reference to the drawings, wherein like numerals are used for like and corresponding parts.

The invention is generally directed to using a guided wave to determine the location of one or more flaws in an inspected object, such as a pipe, rail, etc. In essence, an ultrasonic guided wave signal is launched into the object using conventional ultrasound methods, and the reflected/received signal is sampled to capture a series of individual reflected (guided) waves. The reflected signal is then partitioned into individual waveforms. A time-varying dispersion-modeled reference signal is selected based on the unique geometry of the inspected object, a multiplicity of "theoretical" flaw locations within the object, and the characteristics of the original ultrasonic guided wave. To make a comparison, the reference signal is also generated as a series of partitioned waveforms which model the shape of the waveforms that are expected to be reflected from each theoretical flaw location in the object. The shape of the reflected waveforms is correlated with the shape of the reference waveforms, and a high level of correlation indicates the presence of a real flaw at the theoretical flaw location.

Figure 1:
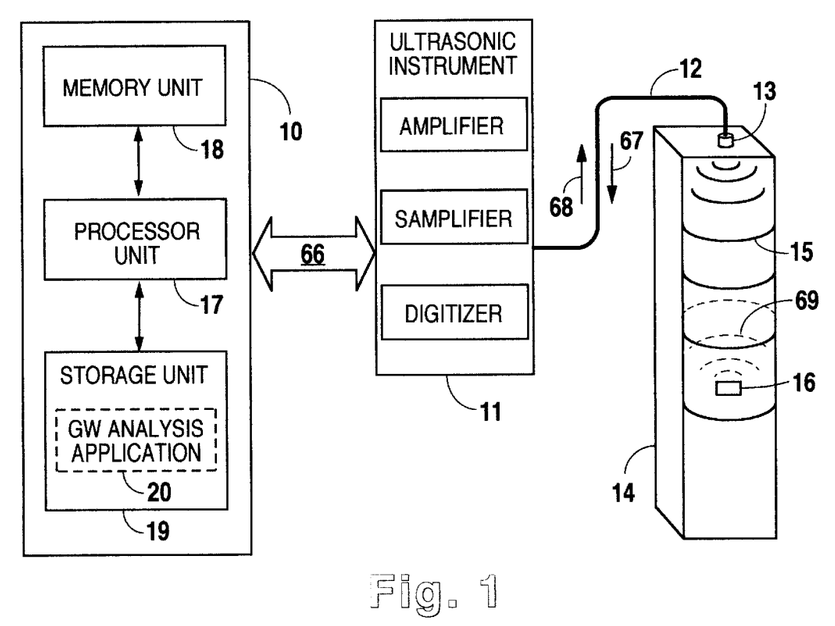
FIG. 1 is system level diagram of an exemplary apparatus for analyzing guided wave inspection signals according to one embodiment of the present invention.

FIG. 1 illustrates an exemplary system for analyzing ultrasonic guided waves according to one exemplary embodiment of the present invention. A data processing apparatus 10, such as one or more high-end desktop computers, workstations, or servers, is coupled to an ultrasonic instrument 11 for receiving ultrasonic guided waves therefrom. The ultrasonic instrument 11 may be any commercially available ultrasonic instrument suitable for the purpose, such as a Krautkramer™ USIP-20. A transmission line 12 connects the ultrasonic instrument 11 to an ultrasonic transducer 13, which is in turn attached to an object 14 to be inspected. The ultrasonic transducer 13 may be any commercially available ultrasonic transducer, such as a piezoelectric transducer, capable of generating and receiving ultrasonic waves. The transmission line 12 carries transmitted electric signals 68 from the ultrasonic instrument 11 to the transducer 13, which cause the transducer 13 to generate narrowband ultrasonic pulses of a predetermined frequency and duration. The ultrasonic pulses propagate through the object 14 as guided waves 15 until they encounter a material boundary or flaw 16. Some of the guided waves 15 are then reflected back from the material boundary or flaw 16 and returned to the transducer 13. The reflected guided waves 69 (dashed lines) are received by the transducer 13 and converted to equivalent received electric signals 67 thereby. These electric signals 67 are thereafter carried by the transmission line 12 back to the ultrasonic equipment 11 for processing. The ultrasonic equipment 11 processes the electric signals by, for example, amplifying, sampling, digitizing, and storing the signals, repeating the process as needed, and provides the processed signals as digital data 66 to the data processing apparatus 10 to be analyzed thereby.

The data processing apparatus 10 has a number of functional components for analyzing the data 66 from the ultrasonic instrument 11 including a processor unit 17, a memory unit 18, and a storage unit 19. The processor unit 17 is responsible for executing various software applications which may reside within the data processing apparatus 10 including an operating system therefor and any data analysis applications residing thereon. The memory unit 18 serves to temporarily store data that may be needed by the processor unit 17 during execution of the various software applications. Long term storage of the various software applications including the operating system and any data analysis software applications as well as raw and/or processed data from the ultrasonic instrument 11 is provided by the storage unit 19. One of the data analysis applications stored in the storage unit 19 and executed by the processor unit 17 within the apparatus 10 is a guided wave analysis application 20 for comparing reference signals with received reflected signals and determining the location of a material boundary or real flaw in an inspected object.

Figure 2:
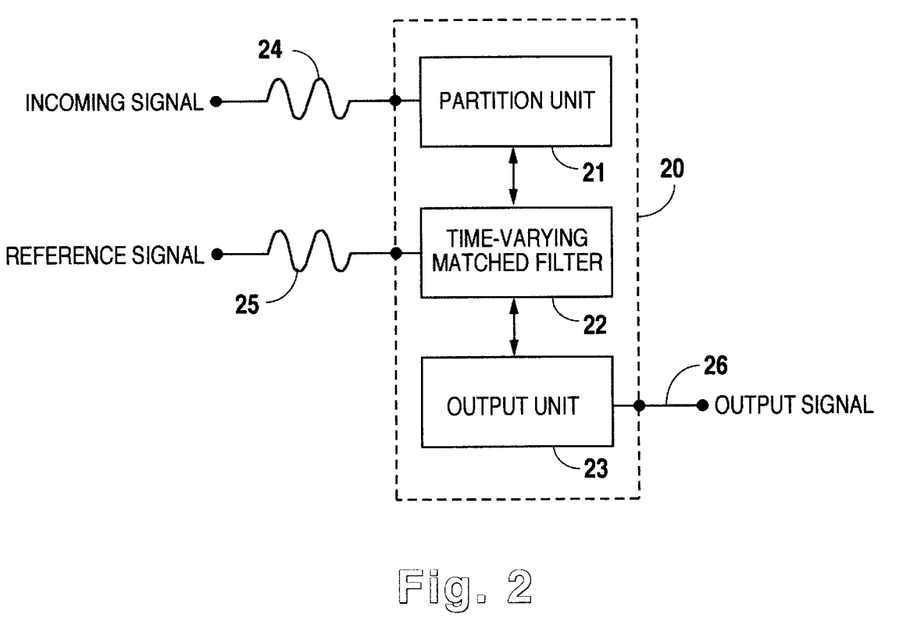
FIG. 2 is a functional block diagram of an exemplary guided wave analysis application according to one embodiment of the present invention.

Referring now to FIG. 2, in one embodiment of the invention, the guided wave analysis application 20 includes a number of program modules for analyzing the received guided wave data including a partition unit 21 module, a time-varying matched filter unit 22 module, and an output unit 23 module. These program modules 21, 22, and 23 operate in conjunction with one another to identify certain desired guided wave modes in the reflected guided waves so as to provide an indication of the location of a possible material boundary and/or real flaw. Each of the program modules 21, 22, and 23 is described below.

The partition unit 21 receives data representing an incoming guided wave signal 24 obtained during a predetermined acquisition period and divides this signal into smaller segments, each segment having one or more guided waves therein. The segments may be defined on a time basis, e.g., according to the start time of each reflected guided wave, or alternatively, at a regular, predetermined time intervals based on the sampling rate of the ultrasonic instrument 11 (see FIG. 1). A typical sampling rate is about 500 kHz, and selection of the sampling rate and size of the segment (i.e., number of samples) may depend on the particular needs of the application. For example, a smaller segment with a high sampling rate may provide higher resolution, but requires more processing capacity, whereas a larger segment (and lower sampling rate) may provide lower resolution, and requires less processing capacity.

In some embodiments, the partition unit may be configured to isolate a predetermined portion of the incoming signal 24 occurring during a certain time interval in order to capture a single reflected wave. The waveform of this single wave may then be compared to the waveforms of the reference signal by the time-varying matched filter 22 to determine a level of correlation.

Operation of the time-varying matched filter 22 is similar to a conventional matched filter in that an incoming signal 24 is compared to the reference signal 25, and the degree of correlation between the two waveforms thereof is provided, after processing by the output unit 23, as an output signal 26. The correlation may also be performed on a wave envelope basis, i.e., based on the shapes outlined by the peaks and troughs of one or more consecutive waves, instead of the amplitudes of the individual waves. In either case, if there is a high degree of correlation (i.e., a match) between the incoming signal 24 and the reference signal 25, then the time-varying matched filter 22 will output a value corresponding to the degree of correlation. Higher values signify a higher degree of correlation.

However, unlike conventional matched filters where the input signals are time invariant, the incoming guided wave signals 24 have waveforms that may change over time due to the dispersive nature of the guided waves. The actual amount of dispersion may depend on a number of factors, including: the desired wave mode (e.g., L(0, 1), L(0, 2), etc.), the geometry (e.g., length, thickness, etc.) and material (e.g., steel, titanium, etc.) of the object through which the guided waves are propagating, the location of the material boundary and/or flaw from which the guided waves are reflected, and the frequency or frequencies of the incident wave. Thus, in accordance with an exemplary embodiment of the invention, the time-varying matched filter 22 must be able to account for the time-varying, dispersive nature of the incoming guided wave signal 24 in order to effectively compare it to the reference signal 25.

In this exemplary embodiment, the reference signal 25 is a time-varying dispersion-modeled reference signal (hence, the term "time-varying" matched filter). Such a time-varying reference signal 25 may then be properly compared to the incoming guided wave signals 24 to more accurately identify the presence of certain guided wave modes therein. The reference signal 25 is generated by the processing apparatus 10 (see FIG. 1) and may be derived, in large part, from the predicted dispersive behavior of selected guided wave modes in objects having known geometries and material properties, the locations of theoretical flaws in such objects, and the characteristics of the incident (transmitted) ultrasonic pulse. For example, the dispersive behavior of L(0, 1) and L(0, 2) mode guided waves in steel pipes, rails, and the like are well known and understood by those of ordinary skill in the art. In addition, the various types and locations of flaws and defects that may occur within those objects are also well known and documented. This information may be compiled and employed to simulate a dispersive wave of a particular mode in an object examined using well known simulation software, such as Disperse™ Software v. 1.0, available from the Imperial College, University of London. The reference signal 25 may then be modeled after the selected simulated dispersive wave mode and generated by the processing apparatus 10. Preferably, the reference signal 25 is generated as one or more time segments of the same size as those selected for the incoming signal 24.

After correlation, the output unit 24 generates an output signal 26 that corresponds to the correlation results received from the time-varying matched filter 22. Generally, the output unit 24 generates a level of output based on degree of correlation. In addition, the output unit 24 may process the correlation result of the time-varying matched filter 22 by, for example, normalizing and performing a Hilbert transform thereon prior to generating the output signal 26.

Figure 3:
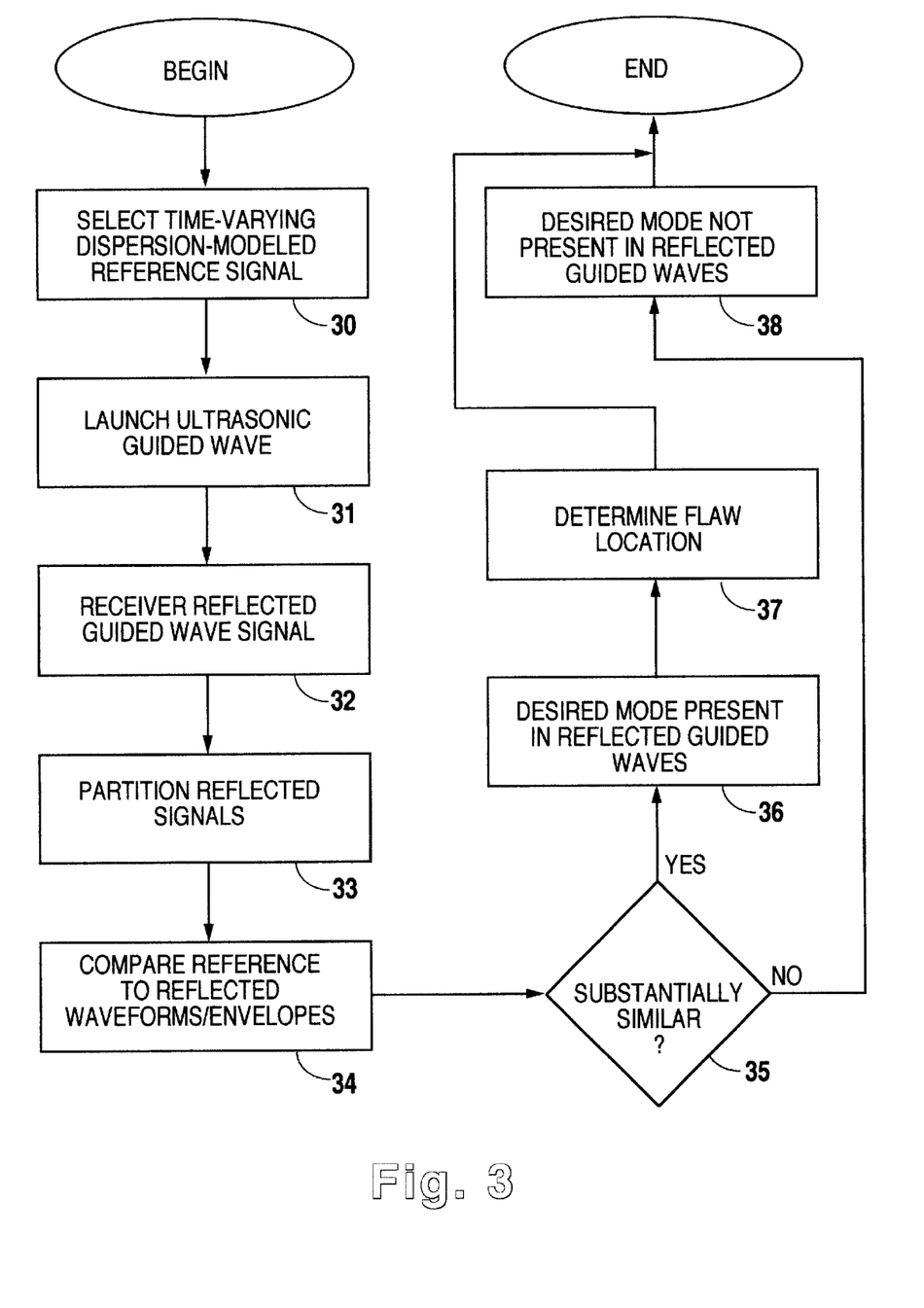
FIG. 3 is flowchart of an exemplary method of identifying guided wave modes according to one embodiment of the present invention.

Referring now to FIG. 3, a method of identifying a guided wave mode according to one embodiment of the present invention is shown in a general sense. At step 30, the particular time-varying dispersion-modeled reference signal can be selected for the desired mode and the particular object to be inspected using the guided wave analysis application. An ultrasonic pulse (guided wave) is launched into the object to be inspected at step 31, typically using an ultrasonic instrument and a transducer. At step 32, guided waves that are reflected off a material boundary or flaw are received by the ultrasonic instrument and the transducer. The reflected guided wave signal is partitioned based on some predetermined segment size related to the extent of dispersion of a particular mode. For instance, 300 points for L(0, 1) in a 4.5 inch OD steel pipe. At step 34, the reflected guided wave signal is compared to the time-varying dispersion-modeled reference signal, either on a waveform basis or on a wave envelope basis. At step 35, it is determined the degree of correlation, or substantial similarity, between the waveforms/envelopes of the reflected signal and the reference signal. In some embodiments, the degree of correlation between the waveforms/envelopes of the two signals should meet or exceed a predefined threshold level of correlation in order to be considered substantially similar. This threshold level would be chosen at a level that avoids detection of harmlessly-small flaws. Such a determination would be based on a safety and economic decision by the pipeline operator. If there is substantial similarity, then it is determined that the desired guided wave mode is present in the reflected guided wave signal at step 36. This information may then be used according to known techniques to determine the location of material boundaries or flaws within the inspected object at step 37. If substantial similarity does not exist, then it is determined that the desired guided wave mode and flaw location is not present in the reflected signal at step 38.

Under the above arrangement, a theoretical flaw is assumed to exist at every point in time where a reflected wave is acquired, and if the acquired reflected wave has a high level of correlation with the reference wave corresponding to that point in time, than the hypothesis or assumption of a flaw at that location in the inspected object is verified. If there is a low level of correlation, then it is assumed that no flaw is detected for the selected guided wave mode. The process can thereafter be repeated using as many different selected guided wave modes as needed to detect other flaws.

Figure 4:
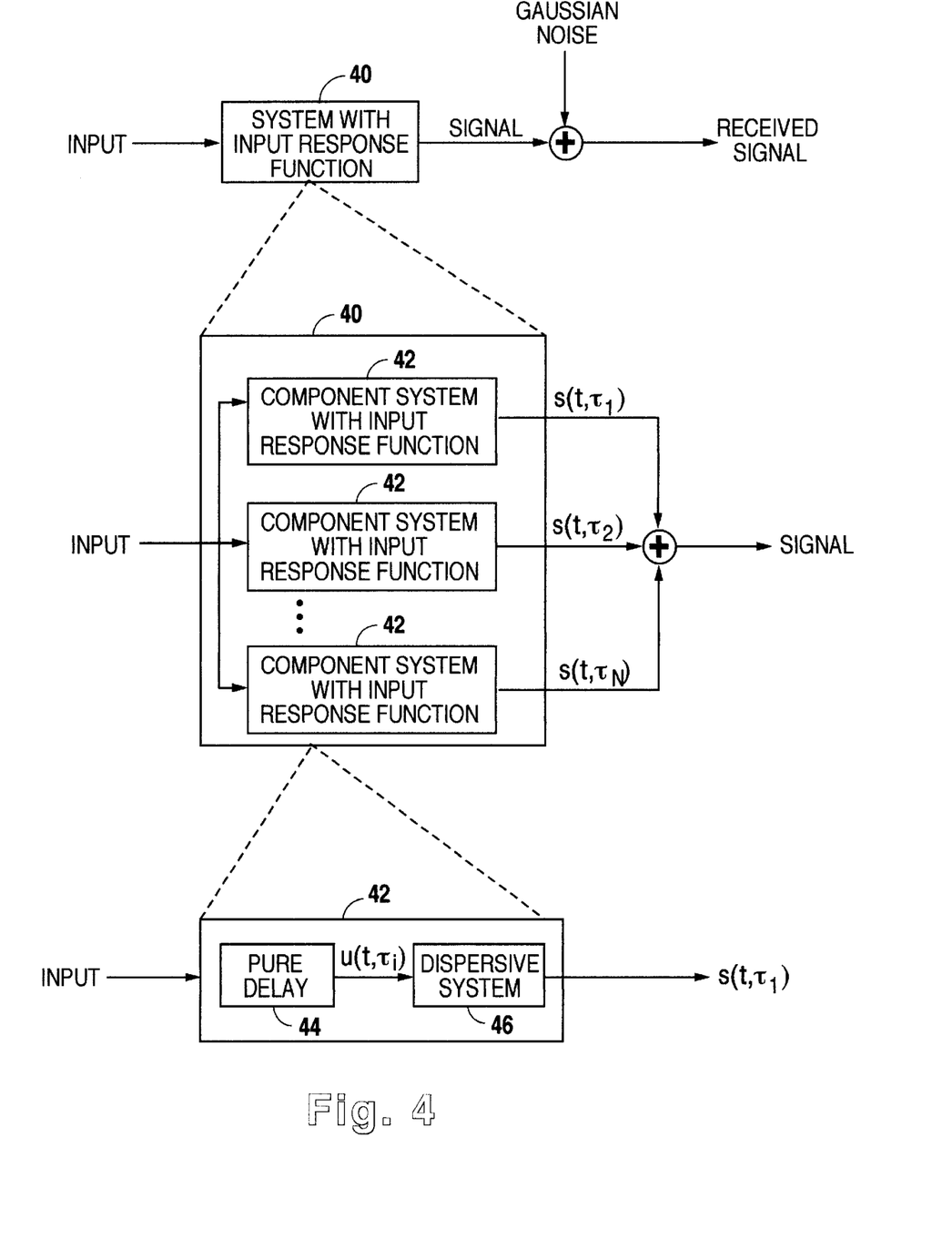
FIG. 4 is a functional block diagram of the system used to derive the time-varying matched filter of the present invention.

The following is a derivation of a mathematical model of the time-varying matched filter of the present invention. Referring to FIG. 4, the objective of such a filter is to be able to detect the components, which are the reflections, of a signal s(t) generated from a system 40 with an impulse response function h(t), and an input u(t). The signal s(t) can be given by the well-known convolution integral:

$$s(t) = \int_{-\infty}^{t} h(t-\sigma)u(\sigma)d\sigma \quad (1)$$

(See, e.g., Oppenheim, A. V., and Schafer, R. W., *Discrete-Time Signal Processing*, Prentice Hall, Englewood Cliffs, N.J. 1989.)

The system 40 can be decomposed as shown into several component systems 42, each having an impulse response function h(t, $\tau_i$), as expressed by the following summation:

$$h(t) = \sum_{i=0}^{N-1} h(t, \tau_i) \quad (2)$$

Each component system 42 can be further decomposed into a cascade composed of a pure delay 44, having a transfer function $\delta(t-\tau_i)$, followed by a dispersive system 46 having an impulse response function $h_i(t)$, as shown.

Figure 7:
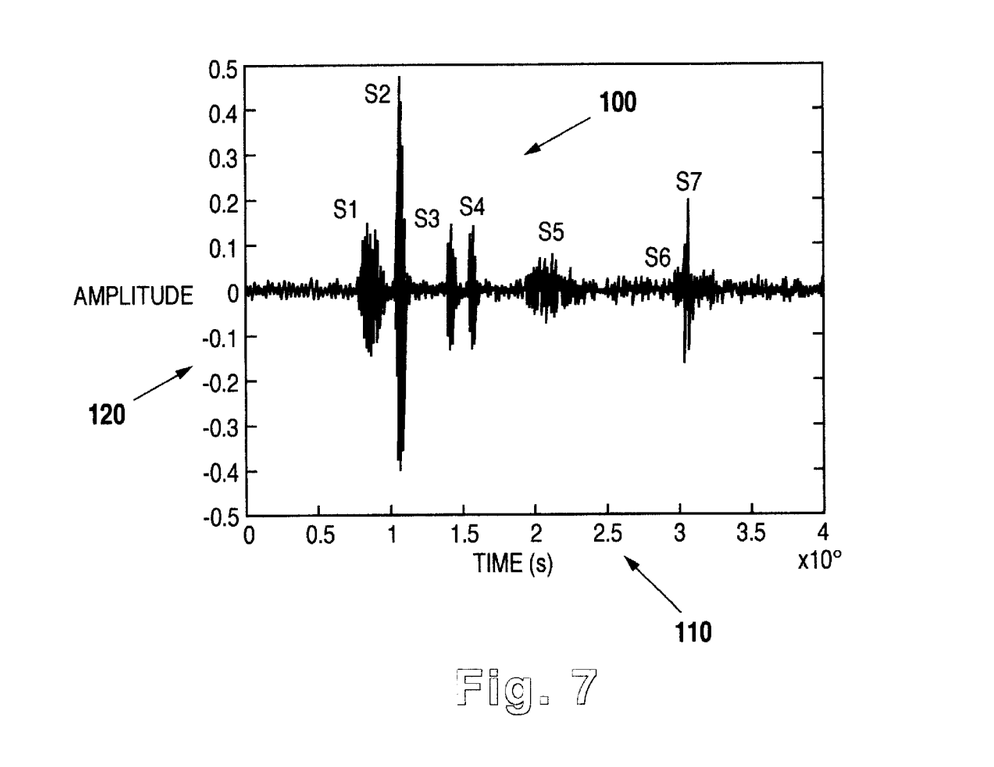
FIG. 7 is a plot of a simulated inspection signal containing reflections of L(0, 1) and L(0, 2) guided wave modes.

It follows that h(t, $\tau_i$)=0 for all t≦$\tau_i$ such that the signal s(t) is comprised of N components and can be expressed as:

$$s(t) = \sum_{i=0}^{N-1} s(t, \tau_i) \quad (3)$$

where $$s(t, \tau_i) = \int_{-\infty}^{t} h(t-\sigma, \tau_i)u(\sigma)d\sigma \quad (4)$$

and $\tau_i$ is the arrival time of the $i^{th}$ component or reflection s(t, $\tau_i$). In other words, s(t, $\tau_i$) denotes a dispersive component/reflection that is present in the signal s(t) beginning only at time t=$\tau_i$. Seven of these are shown in FIG. 7 as $S_1$ through $S_7$. $S_1$, $S_5$, $S_6$ are L(0, 1)'s and $S_2$, $S_3$, $S_4$, $S_7$ are L(0, 2)'s.

The objective is to detect each reflection and estimate the unknown arrival times $\tau_i$ from the received signal r(t), which is given by r(t)=s(t)+n(t), where n(t) is Gaussian noise. Those of ordinary skill in the art can assume that the impulse response function h(t, $\tau_i$) for the component systems 42 is known for all t and $\tau_i$ for the specific geometries and material properties of the inspected objects that carry the guided wave. The input signal u(t) is likewise known from the characteristics of the ultrasonic pulse used to produce reflected waves (i.e., the initiation signal).

As alluded to earlier, the conventional technique for detecting a signal and estimating its arrival time is the matched filter, which performs correlation processing between the received signal r(t) and the desired signal s(t). Normally, the matched filter is time invariant. However, in this case, due to the dispersive nature of guided waves, the desired signal s(t) has been expressed as a function of $\tau_i$ and, therefore, the optimal matched filter should also be time-varying.

Accordingly, the received signal r(t) is passed through a linear time-varying filter with Green's function g(t, $\sigma$) to generate the response y(t) given by:

$$y(t) = \int_{-\infty}^{t} g(t, \sigma) r(\sigma) d\sigma = y_s(t) + y_n(t) \quad (5)$$

where the noise component $y_n(t)$ is given by:

$$y_n(t) = \int_{-\infty}^{t} g(t, \sigma) n(\sigma) d\sigma \quad (6)$$

and the signal component $y_s(t)$ is given by:

$$y_s(t) = \int_{-\infty}^{t} g(t, \sigma) s(\sigma) d\sigma \quad (7)$$

Green's function $g(t, \sigma)$ is the system response at time t to an impulse applied at time $\sigma$. (See, e.g., Stakgold, I., *Green's Function and Boundary Value Problems,* Wiley Press, New York, 1998.)

Using the expression for s(t) in Equation (3), $y_s(t)$ can be written as:

$$y_s(t) = \int_{-\infty}^{t} g(t, \sigma) \sum_{i=0}^{N-1} s(\sigma, \tau_i) d\sigma \quad (8)$$

Commuting the order of integration with summation results in the following:

$$y_s(t) = \sum_{i=0}^{N-1} \int_{-\infty}^{t} g(t, \sigma) s(\sigma, \tau_i) d\sigma \quad (9)$$

It follows from Equation (9) that the signal component $y_s(t)$ can be written as:

$$y_s(t) = \sum_{i=0}^{N-1} y_s(t, \tau_i) \quad (10)$$

The objective in designing a matched filter is to maximize the signal-to-noise ratio for each reflection. (See, e.g., McDonough, R. N., and Whalen, A. D. *Detection of Signals in Noise,* Academic Press, San Diego, 1995.) The signal-to-noise ratio for the $i^{th}$ reflection can be defined by:

$$R(t, \tau_i) = \frac{|y_s(t, \tau_i)|}{r_{yn}(t, t)} \quad (11)$$

at the specific time $t = t_i = \tau_i + T_i$, where $T_i$ is the duration of time over which $s(t, \tau_i)$ is nonzero, and $r_{yn}(t, t)$ can be expressed as:

$$r_{yn}(t,t) = E[y_n(t) y_n(t)] \quad (12)$$

Using the results from Equation (5), the signal-to-noise ratio $R(t, \tau_i)$ defined by Equation 11 will be maximized at $t = t_i = \tau_i + T_i$ if the following is true:

$$g(t, \sigma) = s(\sigma, t - T_i) \quad (13)$$

Thus, by setting Green's function equal to the $i^{th}$ component/reflection of the desired signal s(t), the signal-to-noise ratio $R(t, \tau_i)$ will be maximized. The time-varying matched filter response will then exhibit peaks at $t = t_i = \tau_i + T_i$ that are indicative of the presence of a reflection and its time of arrival.

Note that often the matched filter response will be shifted by $T_i$ such that the peaks in y(t) will align with energy spikes in the received signal r(t).

Following herein is a simulated example showing the performance of the time-varying matched filter of the present invention based on the above model. To implement the time-varying matched filter and evaluate its performance, a simulated guided wave signal r(t) as it propagates within a pipe was created using a computer program. This simulation was produced using mathematical results from Gazis, D. C., *J. Accoust. Soc. Am.* 31, 568–573 (1959), incorporated herein by reference, and the dispersion relationship produced by the Disperse™ software (mentioned above) for a nominal cylinder diameter and wall thickness. This information is normally sufficient to construct the system model $h(t, \tau_i)$ given by Equation (2). A Gaussian-windowed sinusoidal pulse is used for u(t), representing the initial ultrasonic pulse induced in the examined pipe.

Figure 5:
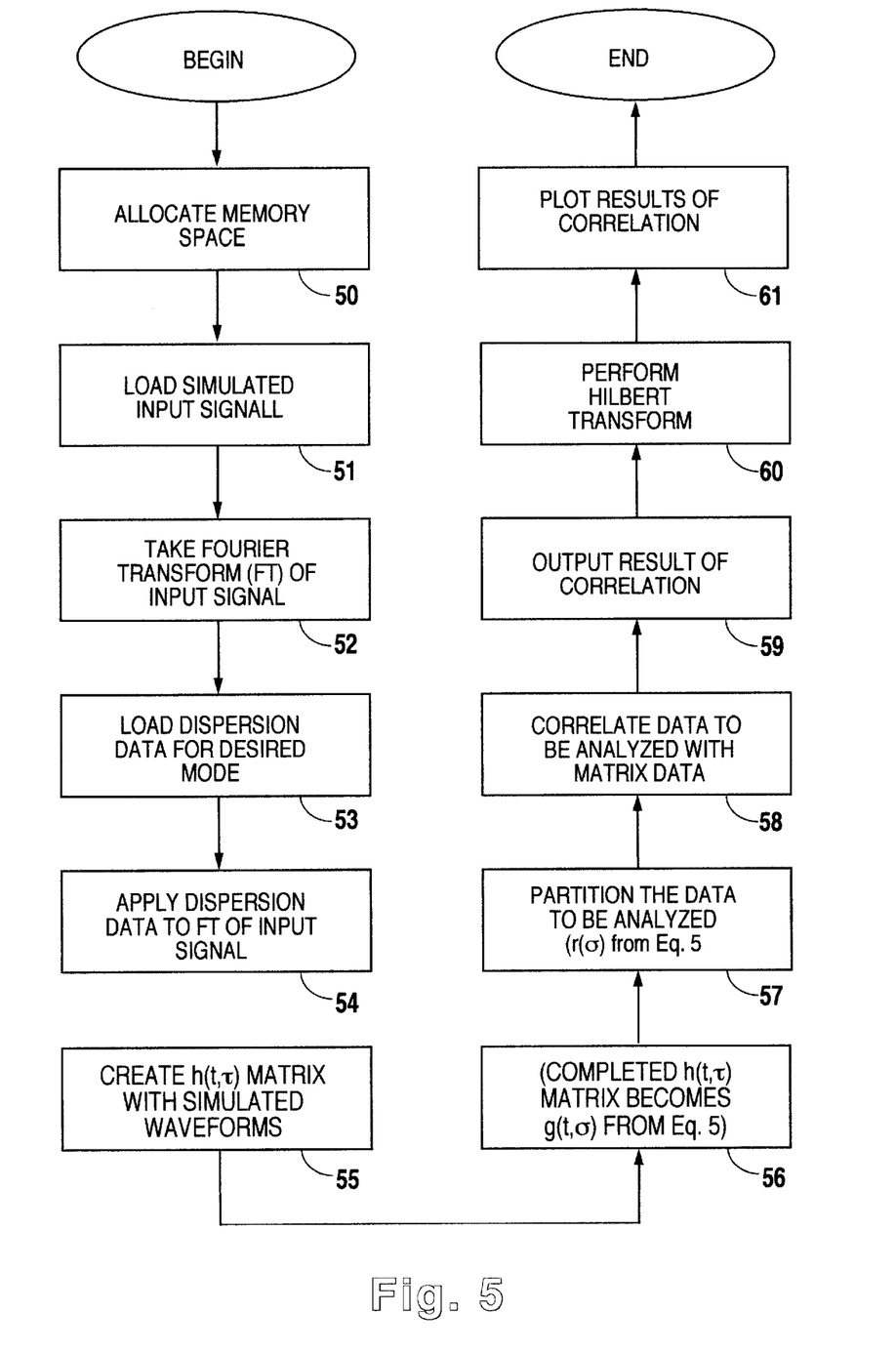
FIG. 5 is a flowchart of an exemplary method of implementing a time-varying matched filter according to one embodiment of the present invention.

A second program, the exemplary steps of which are shown in FIG. 5, was written using Equation (5) to implement the time-varying matched filter of the present invention. At step 50, a sufficient amount of memory space is allocated. A predetermined input signal having the characteristics, such as a narrow frequency band, Gaussian-windowed sinusoid, of an ultrasonic pulse is loaded at step 51. At step 52, a Fourier transform is performed on the input signal. Dispersion data is applied to the Fourier transform of the input signal to simulate a dispersive guided wave propagating through the pipe at step 54. The dispersion data for a pipe is well known and is based on a number of factors including the characteristics of the input signal and the geometry and material properties of the pipe.

Figure 6:
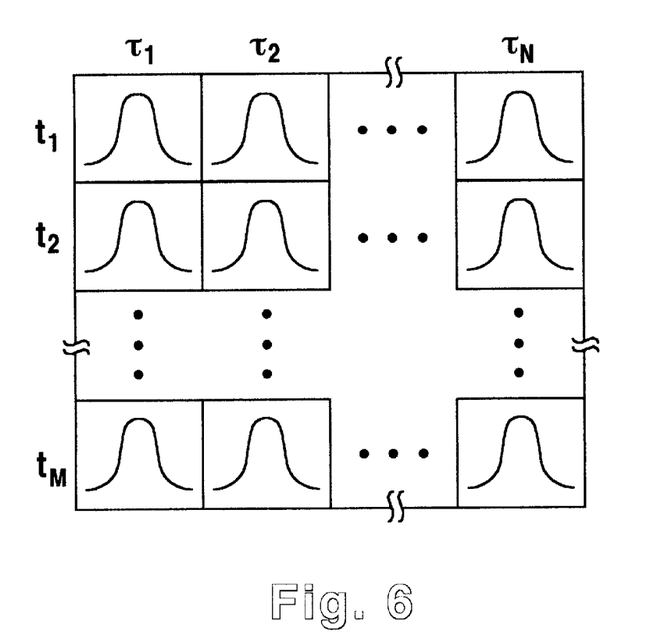
FIG. 6 is a matrix of time-varying dispersion-modeled reference waveforms.

At step 55, a matrix of adequate size is generated for storing the impulse responses $h(t, \tau)$, and is then filled with simulated waveforms. An exemplary matrix is shown in FIG. 6 with M rows and N columns. Each row $t_i$ represents the begin time for the reflections from a particular theoretical flaw, with each subsequent row $t_{i+1}$ representing flaws that are located progressively further and further down the length of the examined object. Each column $\tau_t$ represents the arrival time of the $i^{th}$ reflection associated with a particular reflection start time $t_i$, with each subsequent column $\tau_{t+1}$ representing reflections that arrive progressively later and later in time. Thus, each row $t_i$ in the matrix is associated with a vector of $\tau$'s representing arrival times for reflections that began at time t for that row. The waveforms used to fill the matrix are generated from simulations that use the Fourier transform of the input signal, the reflection begin time t, and the dispersion behavior for the desired guided wave mode. Time t is the time step index in the sampled data. For each time step, the time t is used to generate a reference signal that would have begun at that time. Time t is simply equal to the size of the time step=$t_1-t_0$ or $t_{n-1}-t_n$.

At step 56, the completed $h(t, \tau)$ matrix becomes Green's function $g(t, \sigma)$ in Equation (5). The received guided wave data to be analyzed is then partitioned at step 57 by collecting a vector of the guided wave data corresponding to each time t of the matrix $g(t, \sigma)$ and having the same length as a row of the $g(t, \sigma)$ matrix. This vector of data becomes $r(\sigma)$ in Equation (5).

At step 58, the guided wave data to be analyzed is correlated with the $h(t, \tau)$ (i.e., $g(t, \tau)$) matrix data. More specifically, the correlation is performed by multiplying the appropriate row of the $g(t, \sigma)$ matrix with the corresponding vector $r(\sigma)$ for every time t in the matrix. The result of the correlation, which is y(t) in Equation (5), is provided at step 59. At step 60, a Hilbert transform is performed to remove the sinusoidal nature of the output y(t) and to produce all positive values therefor. The output y(t) for every time t is thereafter plotted at step 61.

FIG. 7 shows the simulated received signal r(t) 100, which includes the simulated mode reflections (i.e., $S_1 \ldots S_7$) along with colored and white noise to create a signal representative of field inspection data. The horizontal axis 110 is time and the vertical axis 120 is the amplitude. Time zero indicates the initial or launch time of the input signal. The various simulated mode reflections of the received signal r(t) 100 are labeled $S_1$ to $S_7$ and represent possible material boundaries and/or flaws.

Figure 8:
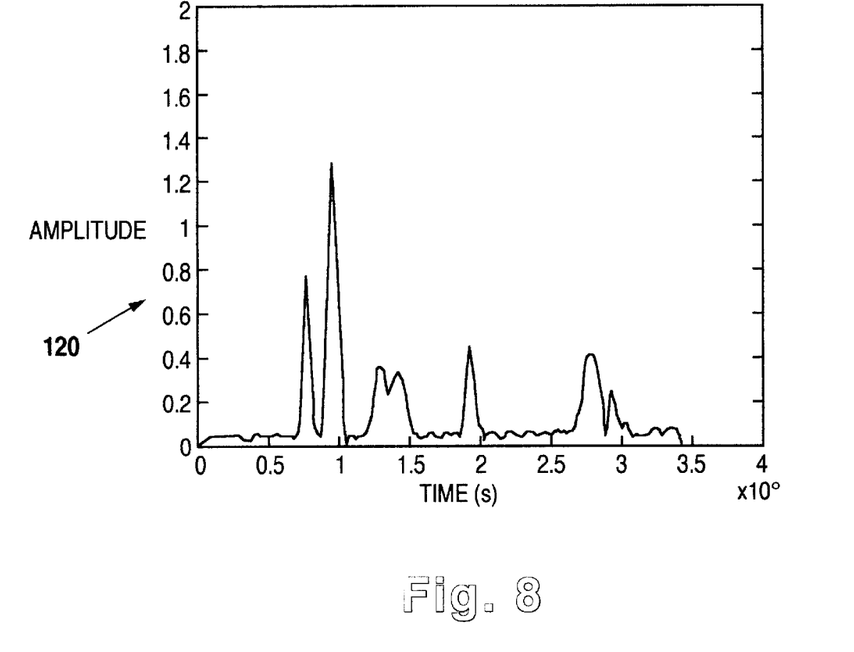
FIG. 8 is a plot of the output of the time-varying matched filter of the present invention biased for the L(0, 1) mode.
Figure 9:
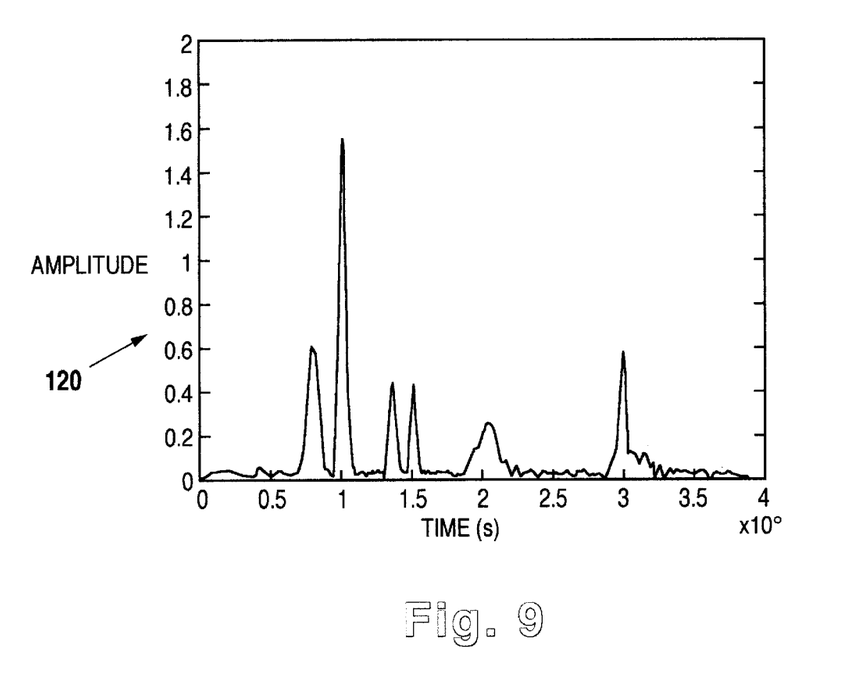
FIG. 9 is a plot of the output of the time-varying matched filter of the present invention biased for the L(0, 2) mode.

The responses $y_i(t)$ given by Equation (5) are shown in FIGS. 8 and 9 for detection of L(0, 1) and L(0, 2) guided wave modes of reflection, respectively. Note that the responses of the time-varying matched filter as shown in FIGS. 8 and 9 have been normalized by the factor:

$$A = \frac{y(\tau_i)}{\int_{-\infty}^{\infty} s^2(t, \tau_i) dt}. \quad (14)$$

In most evaluations involving pipe geometry, L(0, 2) is the preferred mode for inspection because it is nondispersive over a sizeable frequency range. Thus, absolute detection of L(0, 1) mode reflections is important so as to avoid their misinterpretation as L(0, 2) reflections. As shown in FIGS. 8 and 9, both time-varying matched filter responses exhibit peaks in response to the received inspection signal r(t) 100. This is due to the fact that L(0, 1) and L(0, 2) mode reflections have some similarity, especially early in the signal before the L(0, 1) wave has dispersed. However, upon closer examination, it is evident that for the same signal location, the peak of the time-varying matched filter response of FIG. 9 appears sharper. The peak sharpness can be used to identify the particular mode of reflection. Sharper peaks indicate the degree of likelihood that the chosen mode was detected at that point. For this data, both the L(0, 1) and L(0, 2) TVMF's were run. For a particular reflection of interest in the inspection signal, the sharpnesses of the TVMF peaks were compared for the L(0, 1) and L(0, 2) outputs. The sharper of the two indicated which mode the reflection belonged to. Furthermore, the temporal location of the tip of a peak in the time-varying matched filter response can be used to determine the time of arrival for the reflected wave.

Figure 10:
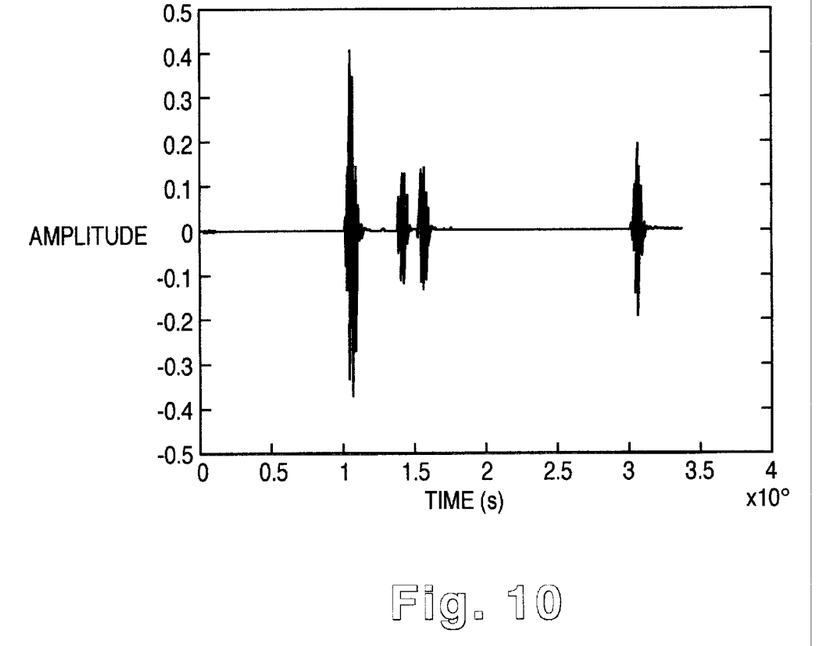
FIG. 10 is a plot of the signal shown in FIG. 7 with the L(0, 2) mode only.
Figure 11:
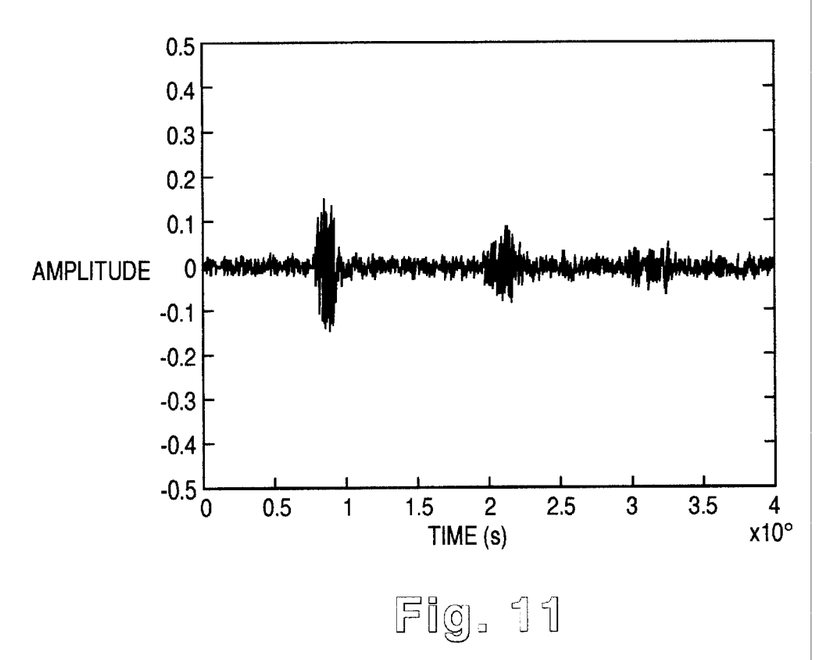
FIG. 11 is a plot of the signal shown in FIG. 7 with the L(0, 1) and remaining noise mode only.

FIG. 10 shows the L(0, 2) reflections as constructed using the dispersion model and parameters generated from the time-varying matched filter response. The L(0, 2) reflections from FIG. 10 were then subtracted from the inspection signal in FIG. 7 to isolate the L(0, 1) reflections and noise, as can be seen in FIG. 11.

TABLE 1 lists the time-of-arrival estimations using the time-varying matched filter for all of the mode reflections in the received inspection signal r(t) 100 shown in FIG. 7. As can be seen, the estimated times of arrival (Estimated $\tau_i$) very closely track the actual time of arrival (Actual $\tau_i$) in this simulation. The result confirms the validity and accuracy of the model of the time-varying matched filter described above.

TABLE 1

| Reflection | Actual $\tau_i$ (ms) | Estimated $\tau_i$ (ms) | Mode of Reflection |
| --- | --- | --- | --- |
| $S_1$ | 0.750 | 0.752 | L(0,1) |
| $S_2$ | 1.000 | 1.003 | L(0,2) |
| $S_3$ | 1.350 | 1.356 | L(0,2) |
| $S_4$ | 1.500 | 1.502 | L(0,2) |
| $S_5$ | 1.900 | 1.910 | L(0,1) |
| $S_6$ | 2.900 | 2.920 | L(0,1) |
| $S_7$ | 3.000 | 3.004 | L(0,2) |

Although the invention has been described with reference to specific embodiments, this description is not meant to be construed in a limited sense. The various modifications of the disclosed embodiments, as well as alternative embodiments of the invention, will become apparent to persons skilled in the art upon reference to the description of the invention. It is, therefore, contemplated that the appended claims will cover such modifications that fall within the scope of the invention, or their equivalents.

What is claimed is:

1. A method for using a selected ultrasonic guided wave having a characteristic to determine a location of a real flaw in an inspected object having a geometry and a multiplicity of theoretical flaw locations, comprising the steps of:

selecting a time-varying dispersion-modeled reference signal associated with the geometry of the inspected object, the multiplicity of theoretical flaw locations within the inspected object, and the characteristic of the guided wave;

launching the selected ultrasonic guided wave into the inspected object;

receiving a reflected signal generated by the interaction of the selected ultrasonic guided wave and the geometry of the inspected object including any real flaw located therein;

comparing the selected time-varying dispersion-modeled reference signal with the received reflected signal;

determining the location of the real flaw in the inspected object if the time-varying dispersion-modeled reference signal resembles the received reflected signal;

wherein the time-varying dispersion-modeled reference signal comprises a plurality of partitioned reference waveforms, and wherein the step of comparing the time-varying dispersion-modeled reference signal with the received reflected signal includes the steps of:

partitioning the received reflected signal according to a time of reception so as to produce a plurality of partitioned reflected signal waveforms; and comparing the plurality of partitioned reflected signal waveforms with the plurality of partitioned reference waveforms to determine a level of correlation.

2. The method of claim 1, wherein each one of the plurality of partitioned reflected signal waveforms has a corresponding reflected signal wave shape, wherein each one of the plurality of partitioned reference waveforms has a corresponding reference signal wave shape, and wherein the step of comparing the plurality of partitioned reflected signal waveforms with the plurality of partitioned reference waveforms to determine a level of correlation includes the step of comparing the corresponding reflected signal wave shape with the corresponding reference signal wave shape.

3. The method of claim 1, wherein each one of the plurality of partitioned reflected signal waveforms has a corresponding reflected signal envelope, wherein each one of the plurality of partitioned reference waveforms has a corresponding reference signal envelope, and wherein the step of comparing the plurality of partitioned reflected signal waveforms with the plurality of partitioned reference waveforms to determine a level of correlation includes the step of comparing the corresponding reflected signal envelope with the corresponding reference signal envelope.

4. The method of claim 1, wherein the step of determining the location of the real flaw in the inspected object if the time-varying dispersion-modeled reference signal is substantially similar to the reflected signal includes the steps of:
   comparing the level of correlation with a predetermined correlation level; and
   providing an indication of the location of the real flaw in the inspected object if the level of correlation is greater than about the predetermined correlation level.

5. The method of claim 1, wherein the step of partitioning the received reflected signal according to a time of reception of each waveform therein so as to produce a plurality of partitioned reflected signal waveforms includes the steps of:
   sampling the received reflected signal at a preselected sampling time interval to obtain a single partitioned reflected signal waveform;
   storing the single partitioned reflected signal waveform; and
   repeating the steps of sampling and storing for a predetermined acquisition time period.

6. A method for using a selected ultrasonic guided wave having a characteristic to determine a location of a real flaw in an inspected object having a geometry and a multiplicity of theoretical flaw locations, comprising the steps of:
   selecting a time-varying dispersion-modeled reference signal associated with the geometry of the inspected object, the multiplicity of theoretical flaw locations within the inspected object, and the characteristic of the guided wave;
   launching the selected ultrasonic guided wave into the inspected object;
   receiving a reflected signal generated by the interaction of the selected ultrasonic guided wave and the geometry of the inspected object including any real flaw located therein;
   comparing the selected time-varying dispersion-modeled reference signal with the received reflected signal;
   determining the location of the real flaw in the inspected object if the time-varying dispersion-modeled reference signal resembles the received reflected signal;
   wherein the step of comparing the time-varying dispersion-modeled reference signal with the received reflected signal includes the steps of:
      partitioning the received reflected signal according to a time of reception so as to produce a plurality of partitioned reflected signal waveforms;
      selecting a single partitioned reflected signal waveform from the plurality of partitioned reflected signal waveforms associated with a predetermined time of acquisition;
      generating a single partitioned reference signal waveform associated with the predetermined time of acquisition; and
      comparing the single partitioned reflected signal waveform with the single partitioned reference waveform to determine a level of correlation.

7. The method of claim 6, wherein the step of determining the location of the real flaw in the inspected object if the time-varying dispersion-modeled reference signal is substantially similar to the received reflected signal includes the steps of:
   comparing the level of correlation with a predetermined correlation level; and
   providing an indication of the location of the real flaw in the inspected object if the level of correlation is greater than about the predetermined correlation level.

8. A method for using a selected ultrasonic guided wave having a characteristic to determine a location of a real flaw in an inspected object having a geometry and a multiplicity of theoretical flaw locations, comprising the steps of:
   selecting a time-varying dispersion-modeled reference signal associated with the geometry of the inspected object, the multiplicity of theoretical flaw locations within the inspected object, and the characteristic of the guided wave;
   launching the selected ultrasonic guided wave into the inspected object;
   receiving a reflected signal generated by the interaction of the selected ultrasonic guided wave and the geometry of the inspected object including any real flaw located therein;
   comparing the selected time-varying dispersion-modeled reference signal with the received reflected signal;
   determining the location of the real flaw in the inspected object if the time-varying dispersion-modeled reference signal resembles the received reflected signal;
   wherein the time-varying dispersion-modeled reference signal represents one of a plurality of reference propagation modes, and wherein the step of comparing the time-varying dispersion-modeled reference signal with the received reflected signal includes the steps of:
      selecting at least one reference propagation mode from the plurality of reference propagation modes, wherein the selected at least one reference propagation mode includes a corresponding plurality of partitioned reference signal waveforms;
      partitioning the received reflected signal according to a time of reception so as to produce a plurality of partitioned reflected signal waveforms; and
      comparing the plurality of partitioned reflected signal waveforms with the corresponding plurality of partitioned reference waveforms to determine a level of correlation.

9. An apparatus for using a selected ultrasonic guided wave having a characteristic to determine a location of a real flaw in an inspected object having a geometry and a multiplicity of theoretical flaw locations, comprising:
   a means for selecting a time-varying dispersion-modeled reference signal associated with the geometry of the inspected object, the multiplicity of theoretical flaw locations therein, and the characteristic of the selected ultrasonic guided wave;
   a means for launching the selected ultrasonic guided wave into the inspected object;
   a means for receiving a reflected signal generated by the interaction of the selected ultrasonic guided wave and the geometry of the inspected object including any real flaw located therein;
   a means for comparing the time-varying dispersion-modeled reference signal with the received reflected signal;
   a means for determining the location of the real flaw in the inspected object if the time-varying dispersion-modeled reference signal resembles the received reflected signal;
   wherein the means for comparing the time-varying dispersion-modeled reference signal with the received reflected signal includes a means for correlating the time-varying dispersion-modeled reference signal with the received reflected signal.

10. An apparatus for using a selected ultrasonic guided wave having a characteristic to determine a location of a real flaw in an inspected object having a geometry and a multiplicity of theoretical flaw locations, comprising:
- a means for selecting a time-varying dispersion-modeled reference signal associated with the geometry of the inspected object, the multiplicity of theoretical flaw locations therein, and the characteristic of the selected ultrasonic guided wave;
- a means for launching the selected ultrasonic guided wave into the inspected object;
- a means for receiving a reflected signal generated by the interaction of the selected ultrasonic guided wave and the geometry of the inspected object including any real flaw located therein;
- a means for comparing the time-varying dispersion-modeled reference signal with the received reflected signal;
- a means for determining the location of the real flaw in the inspected object if the time-varying dispersion-modeled reference signal resembles the received reflected signal;
- wherein the time-varying dispersion-modeled reference signal comprises a plurality of partitioned reference waveforms, and wherein the means for comparing the time-varying dispersion-modeled reference signal with the received reflected signal further includes a means for partitioning the received reflected signal according to a time of reception so as to produce a plurality of partitioned reflected signal waveforms.

11. The apparatus of claim 10, wherein each one of the plurality of partitioned reflected signal waveforms has a corresponding reflected signal wave shape, wherein each one of the plurality of partitioned reference waveforms has a corresponding reference signal wave shape, and wherein the means for comparing the plurality of partitioned reflected signal waveforms with the plurality of partitioned reference waveforms to determine a level of correlation includes a means for comparing the corresponding received reflected signal wave shape with the corresponding reference signal wave shape.

12. The apparatus of claim 10, wherein each one of the plurality of partitioned reflected signal waveforms has a corresponding reflected signal envelope, wherein each one of the plurality of partitioned reference waveforms has a corresponding reference signal envelope, and wherein the means for comparing the plurality of partitioned reflected signal waveforms with the plurality of partitioned reference waveforms to determine a level of correlation includes a means for comparing the corresponding reflected signal envelope with the corresponding reference signal envelope.

13. An apparatus for using a selected ultrasonic guided wave having a characteristic to determine a location of a real flaw in an inspected object having a geometry and a multiplicity of theoretical flaw locations, comprising:
- a means for selecting a time-varying dispersion-modeled reference signal associated with the geometry of the inspected object, the multiplicity of theoretical flaw locations therein, and the characteristic of the selected ultrasonic guided wave;
- a means for launching the selected ultrasonic guided wave into the inspected object;
- a means for receiving a reflected signal generated by the interaction of the selected ultrasonic guided wave and the geometry of the inspected object including any real flaw located therein;
- a means for comparing the time-varying dispersion-modeled reference signal with the received reflected signal;
- a means for determining the location of the real flaw in the inspected object if the time-varying dispersion-modeled reference signal resembles the received reflected signal;
- wherein the means for determining the location of the real flaw in the inspected object if the time-varying dispersion-modeled reference signal resembles the received reflected signal includes a means for comparing a level of correlation between the time-varying dispersion-modeled reference signal and the received reflected signal with a predetermined correlation level, wherein a level of correlation approximately greater than or equal to the predetermined correlation level provides an indication of the location of the real flaw in the inspected object.

14. The apparatus of claim 10, wherein the means for partitioning the received reflected signal according to a time of reception so as to produce a plurality of partitioned reflected signal waveforms includes:
- means for sampling the reflected signal at a preselected sampling time interval to obtain a single partitioned reflected signal waveform;
- means for storing the single partitioned reflected signal waveform; and
- means for repeating the steps of sampling and storing for a predetermined acquisition time period.

15. An apparatus for using a selected ultrasonic guided wave having a characteristic to determine a location of a real flaw in an inspected object having a geometry and a multiplicity of theoretical flaw locations, comprising:
- a means for selecting a time-varying dispersion-modeled reference signal associated with the geometry of the inspected object, the multiplicity of theoretical flaw locations therein, and the characteristic of the selected ultrasonic guided wave;
- a means for launching the selected ultrasonic guided wave into the inspected object;
- means for receiving a reflected signal generated by the interaction of the selected ultrasonic guided wave and the geometry of the inspected object including any real flaw located therein;
- a means for comparing the time-varying dispersion-modeled reference signal with the received reflected signal;
- a means for determining the location of the real flaw in the inspected object if the time-varying dispersion-modeled reference signal resembles the received reflected signal;
- wherein the means for comparing the time-varying dispersion-modeled reference signal with the received reflected signal includes:
  - means for partitioning the received reflected signal according to a time of reception so as to produce a plurality of partitioned reflected signal waveforms;
  - means for selecting a single partitioned reflected signal waveform from the plurality of partitioned reflected signal waveforms associated with a predetermined time of acquisition;
  - means for generating a single partitioned reference signal waveform associated with the predetermined time of acquisition; and means for comparing the single partitioned reflected signal waveform with the single partitioned reference waveform to determine the level of correlation.

16. The apparatus of claim 15, wherein the means for determining the location of the real flaw in the inspected object if the time-varying dispersion-modeled reference signal is substantially similar to the received reflected signal includes:

means for comparing the level of correlation with a predetermined correlation level; and means for providing an indication of the location of the real flaw in the inspected object if the level of correlation is greater than about the predetermined correlation level.

17. An apparatus for using a selected ultrasonic guided wave having a characteristic to determine a location of a real flaw in an inspected object having a geometry and a multiplicity of theoretical flaw locations, comprising:

a means for selecting a time-varying dispersion-modeled reference signal associated with the geometry of the inspected object, the multiplicity of theoretical flaw locations therein, and the characteristic of the selected ultrasonic guided wave;

means for launching the selected ultrasonic guided wave into the inspected object;

means for receiving a reflected signal generated by the interaction of the selected ultrasonic guided wave and the geometry of the inspected object including any real flaw located therein;

a means for comparing the time-varying dispersion-modeled reference signal with the received reflected signal;

a means for determining the location of the real flaw in the inspected object if the time-varying dispersion-modeled reference signal resembles the received reflected signal;

wherein the time-varying dispersion-modeled reference signal represents one of a plurality of reference propagation modes, and wherein the means for comparing the time-varying dispersion-modeled reference signal with the received reflected signal includes:

means for selecting at least one reference propagation mode from the plurality of reference propagation modes, wherein the selected at least one reference propagation mode includes a corresponding plurality of partitioned reference signal waveforms;

means for partitioning the reflected signal according to a time of reception so as to produce a plurality of partitioned reflected signal waveforms; and means for comparing the plurality of partitioned reflected signal waveforms with the corresponding plurality of partitioned reference waveforms to determine a level of correlation.

18. The apparatus of claim 9, wherein the means for correlating the time-varying dispersion-modeled reference signal with the received reflected signal includes a time-varying matched filter module executed on the apparatus.

19. The apparatus of claim 10, wherein the means for partitioning the reflected signal according to a time of reception so as to produce a plurality of partitioned reflected signal waveforms includes a partition module executed on the apparatus.

* * * * *